US008680096B2

(12) United States Patent
Auger et al.

(10) Patent No.: US 8,680,096 B2
(45) Date of Patent: Mar. 25, 2014

(54) DIPHENYL-PYRAZOLOPYRIDINE DERIVATIVES, PREPARATION THEREOF, AND USE THEREOF AS NUCLEAR RECEPTOR NOT MODULATORS

(75) Inventors: Florian Auger, Paris (FR); Luc Even, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 13/513,497

(22) PCT Filed: Dec. 3, 2010

(86) PCT No.: PCT/FR2010/052605

§ 371 (c)(1), (2), (4) Date: Jun. 1, 2012

(87) PCT Pub. No.: WO2011/067544

PCT Pub. Date: Jun. 9, 2011

(65) Prior Publication Data

US 2012/0245164 A1 Sep. 27, 2012

(30) Foreign Application Priority Data

Dec. 4, 2009 (FR) ..................................... 09 58651

(51) Int. Cl.

| | |
|---|---|
| ***A61K 31/5377*** | (2006.01) |
| ***A61P 19/10*** | (2006.01) |
| ***A61P 35/00*** | (2006.01) |
| ***A61P 25/16*** | (2006.01) |
| ***A61P 25/24*** | (2006.01) |
| ***A61P 25/30*** | (2006.01) |
| ***A61P 29/00*** | (2006.01) |
| ***C07D 471/04*** | (2006.01) |

(52) U.S. Cl.

USPC .......... 514/233.2; 514/300; 546/13; 546/121; 544/127

(58) Field of Classification Search

USPC ........... 514/233.2, 300; 546/13, 121; 544/127

See application file for complete search history.

(56) References Cited

U.S. PATENT DOCUMENTS

2013/0023554 A1* 1/2013 Auger et al. .................. 514/300

FOREIGN PATENT DOCUMENTS

| | | | |
|---|---|---|---|
| FR | 2928921 | A1 | 9/2009 |
| WO | WO2008/034974 | A1 | 3/2008 |

OTHER PUBLICATIONS

International Search Report dated Feb. 11, 2011 issued in PCT/FR2010/052605.

* cited by examiner

*Primary Examiner* — Niloofar Rahmani

(74) *Attorney, Agent, or Firm* — Scully, Scott, Murphy & Presser, P.C.

(57) ABSTRACT

The invention relates to a formula (I), in which R is a hydrogen or halogen atom or a (C1-C6)alkyl group; X is one or more substituents selected from a hydrogen or halogen atom, a (C1-C6)alkyl, halo(C1-C6)alkyl, (C1-C6)alkoxy, halo(C1-C6)alkoxy, cyano, hydroxy, or hydroxy(C1-C6)alkyl group; Y is a hydrogen or halogen atom or a (C1-C6)alkyl group; R1 is an NR2R3 or OR4 group; R2 and R3 independently are a hydrogen atom, a (C1-C6)alkyl, hydroxy(C1-C6)alkyl or oxo(C1-C6)alkyl group or R2 and R3, together with the nitrogen atom supporting the same, form a heterocycle optionally substituted by a (C1-C6)alkyl, hydroxy or oxo group; and R4 is a (C1-C6)alkyl, hydroxy(C1-C6)alkyl, or oxo(C1-C6)alkyl group, in the base or acid addition salt state. Said formula can be used therapeutically for treating or preventing diseases linked to the nuclear receptors Nurr-1, also known as NR4A2, NOT, TINUR, RNR-1, and HZF3.

8 Claims, No Drawings

DIPHENYL-PYRAZOLOPYRIDINE DERIVATIVES, PREPARATION THEREOF, AND USE THEREOF AS NUCLEAR RECEPTOR NOT MODULATORS

The present invention relates to diphenylpyrazolopyridine derivatives, to their preparation and to their therapeutic use in the treatment or prevention of diseases involving the Nurr-1 nuclear receptors, also known as NR4A2, NOT, T1NUR, RNR-1 and HZF3.

One subject of the present invention is the compounds of formula (I):

(I)

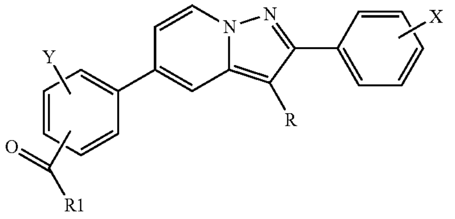

in which:

R represents a hydrogen or halogen atom or a group (C1-C6) alkyl;

X represents one or more substituents chosen from a hydrogen or halogen atom and a group (C1-C6)alkyl, halo(C1-C6)alkyl, (C1-C6)alkoxy, halo(C1-C6)alkoxy, cyano, hydroxyl or hydroxy(C1-C6)alkyl;

Y represents a hydrogen or halogen atom or a group (C1-C6) alkyl;

R1 represents a group NR2R3 or OR4;

R2 and R3 represent, independently of each other, a hydrogen atom or a group (C1-C6)alkyl, hydroxy(C1-C6)alkyl or oxo(C1-C6)alkyl, or alternatively R2 and R3 form, with the nitrogen atom that bears them, a heterocycle optionally substituted with a group (C1-C6)alkyl, hydroxyl or oxo, R4 represents a group (C1-C6)alkyl, hydroxy(C1-C6)alkyl or oxo(C1-C6)alkyl, in the form of base or of acid-addition salt.

The compounds of formula (I) may comprise one or more asymmetric carbon atoms. They may thus exist in the form of enantiomers or diastereoisromers. These enantiomers and diastereoisomers, and also mixtures thereof, including racemic mixtures, form part of the invention.

The compounds of formula (I) may exist in the form of bases or of acid-addition salts. Such addition salts form part of the invention.

These salts may be prepared with pharmaceutically acceptable acids, but the salts of other acids that are useful, for example, for purifying or isolating the compounds of fottuula (I) also form part of the invention.

The compounds of formula (I) may also exist in the form of hydrates or solvates, namely in the form of associations or combinations with one or more water molecules or with a solvent. Such hydrates and solvates also form part of the invention.

In the context of the present invention, the following definitions apply:

- a group ($C_x$-$C_t$): a group comprising between x and t carbon atoms;
- a halogen atom: a fluorine, a chlorine, a bromine or an iodine;
- an alkyl group: a linear, branched or cyclic, saturated aliphatic group, optionally substituted with a linear, branched or cyclic, saturated alkyl group. Examples that may be mentioned include methyl, ethyl, propyl, isopropyl, butyl, isobutyl, tert-butyl, cyclopropyl, cyclobutyl, cyclopentyl, cyclohexyl, methylcyclopropyl, cyclo-propylmethyl, etc. groups;
- an alkoxy group: a radical —O-alkyl in which the alkyl group is as defined previously;
- a haloalkyl group: an alkyl group substituted with one or more identical or different halogen atoms. Examples that may be mentioned include the groups $CF_3$, $CH_2CF_3$, $CHF_2$ and $CCl_3$;
- a hydroxyalkyl group: an alkyl group substituted with a hydroxyl group; examples that may be mentioned include $CH_2OH$, $CH_2CH_2OH$, etc.;
- an oxoalkyl group: an alkyl group substituted with an oxo group (C═O); examples that may be mentioned include $CH_3CO$, $CH_3COCH_2$, etc.;
- a haloalkoxy group: a radical —O-alkyl in which the alkyl group is as defined previously and substituted with one or more identical or different halogen atoms. Examples that may be mentioned include the groups $OCF_3$, $OCHF_2$ and $OCCl_3$;
- an aryl group: a monocyclic or bicyclic aromatic group comprising from 6 to 10 atoms.

Examples of aryl groups that may be mentioned include phenyl and naphthyl;

- a heterocyclic group: a saturated, nitrogenous, optionally bridged cyclic group, comprising between 5 and 9 carbon atoms, at least one nitrogen atom and optionally comprising between 1 and 3 additional heteroatoms, such as oxygen, nitrogen or sulfur. Mention may be made especially of piperidyl, piperazinyl, pyrrolidinyl, morpholinyl, etc. groups.

Among the compounds of formula (I) that are subjects of the invention, a first group of compounds is formed by the compounds for which:

R represents a hydrogen or chlorine atom,

X represents one or more substituents chosen from a halogen atom and a group (C1-C6)alkyl, halo(C1-C6)alkyl, (C1-C6)alkoxy, halo(C1-C6)alkoxy or cyano, Y represents a hydrogen atom, a halogen atom or a group (C1-C6)alkyl;

R1 represents a group OR4,

R4 represents a methyl group, in the form of base or of acid-addition salt.

Among the compounds of formula (I) that are subjects of the invention, a second group of compounds is formed by the compounds for which:

R represents a hydrogen or chlorine atom,

X represents one or more substituents chosen from a chlorine or fluorine atom and a methyl, trifluoromethyl, methoxy, trifluoromethoxy or cyano group, Y represents a hydrogen, chlorine or fluorine atom or a methyl group, R1 represents a group OR4, R4 represents a methyl group, in the fotin of base or of acid-addition salt.

Among the compounds of formula (I) that are subjects of the invention, a third group of compounds is formed by the compounds for which:

R represents a hydrogen or chlorine atom,

X represents one or more substituents chosen from a halogen atom and a group (C1-C6)alkyl, halo(C1-C6)alkyl, (C1-C6)alkoxy, halo(C1-C6)alkoxy or cyano, Y represents a hydrogen atom, a halogen atom or a group (C1-C6)alkyl;

R1 represents a group NR2R3,

R2 and R3 represent, independently of each other, a hydrogen atom or a methyl, ethyl, isopropyl or cyclopropyl group, or alternatively R2 and R3 form, with the nitrogen atom that bears them, a morpholinyl or pyrrolidinyl group optionally substituted with a hydroxyl group, in the form of base or of acid-addition salt.

Among the compounds of formula (I) that are subjects of the invention, a fourth group of compounds is formed by the compounds for which:

R represents a hydrogen or chlorine atom,

X represents one or more substituents chosen from a chlorine or fluorine atom and a methyl, trifluoromethyl, methoxy, trifluoromethoxy or cyano group, Y represents a hydrogen or chlorine atom or a methyl group, R1 represents a group NR2R3, R2 and R3 represent, independently of each other, a hydrogen atom or a methyl, ethyl, isopropyl or cyclopropyl group, or alternatively R2 and R3 form, with the nitrogen atom that bears them, a morpholinyl or pyrrolidinyl group optionally substituted with a hydroxyl group, in the form of base or of acid-addition salt.

The combinations of groups one to four as defined above also form part of the invention.

Among the compounds of formula (I) that are subjects of the invention, mention may be made especially of the following compounds:

Methyl 3-[2-(4-chlorophenyl)pyrazolo[1,5-a]pyridin-5-yl]benzoate

3-[2-(4-Chlorophenyl)pyrazolo[1,5-a]pyridin-5-yl]benzamide

3-[2-(4-Chlorophenyl)pyrazolo[1,5-c]pyridin-5-yl]-N,N-dimethylbenzamide

3-[2-(4-Chlorophenyl)pyrazolo[1,5-a]pyridin-5-yl]-N-methylbenzamide

Methyl 3-[2-(4-fluorophenyl)pyrazolo[1,5-a]pyridin-5-yl]benzoate

3-[2-(4-Fluorophenyl)pyrazolo[1,5-c]pyridin-5-yl]-N-methylbenzamide

3-[2-(4-Fluorophenyl)pyrazolo[1,5-a]pyridin-5-yl]-N-isopropylbenzamide

3-[2-(4-Fluorophenyl)pyrazolo[1,5-c]pyridin-5-yl]-N,N-dimethylbenzamide

{3-[2-(4-Fluorophenyl)pyrazolo[1,5-c]pyridin-5-yl]phenyl}morpholin-4-yl-methanone 3-[2-(4-Fluorophenyl)pyrazolo[1,5-a]pyridin-5-yl]-2,N-dimethylbenzamide 2-Chloro-5-[2-(4-fluorophenyl)pyrazolo[1,5-a]pyridin-5-yl]-N-methylbenzamide 4-Chloro-3-[2-(4-fluorophenyl)pyrazolo[1,5-a]pyridin-5-yl]-N-methylbenzamide 3-[2-(4-Fluorophenyl)pyrazolo[1,5-a]pyridin-5-yl]-4,N-dimethylbenzamide 2-Fluoro-4-[2-(4-fluorophenyl)pyrazolo[1,5-c]pyridin-5-yl]-N-methylbenzamide N-Cyclopropyl-3-[2-(4-fluorophenyl)pyrazolo[1,5-a]pyridin-5-yl]benzamide {3-[2-(4-Fluorophenyl)pyrazolo[1,5-c]pyridin-5-yl]phenyl}pyrrolidin-1-ylmethanone 3-[2-(2,6-Difluorophenyl)pyrazolo[1,5-c]pyridin-5-yl]-methylbenzamide 3-[2-(2-Fluorophenyl)pyrazolo[1,5-a]pyridin-5-yl]-N-methylbenzamide N-Methyl-3-[2-(4-trifluoromethylphenyl)pyrazolo[1,5-a]pyridin-5-yl]benzamide 4-[2-(4-Fluorophenyl)pyrazolo[1,5-a]pyridin-5-yl]-N-methylbenzamide 2-[2-(4-Fluorophenyl)pyrazolo[1,5-c]pyridin-5-yl]-N-methylbenzamide {3-[2-(4-Fluorophenyl)pyrazolo[1,5-a]pyridin-5-yl]phenyl}-(3-hydroxypyrrolidin-1-yl)methanone 3-[2-(2,4-Difluorophenyl)pyrazolo[1,5-a]pyridin-5-yl]-N-methylbenzamide N-Methyl-3-[2-(4-trifluoromethoxyphenyl)pyrazolo[1,5-c]pyridin-5-yl]benzamide 3-[2-(3,4-Difluorophenyl)pyrazolo[1,5-c]pyridin-5-yl]-N-methylbenzamide 3-[2-(3,5-Difluorophenyl)pyrazolo[1,5-c]pyridin-5-yl]-N-methylbenzamide 3-[2-(3-Fluorophenyl)pyrazolo[1,5-a]pyridin-5-yl]-N-methylbenzamide N-Methyl-3-(2-p-tolylpyrazolo[1,5-a]pyridin-5-yl)benzamide 3-[2-(4-Methoxyphenyl)pyrazolo[1,5-a]pyridin-5-yl]-N-methylbenzamide 3-[2-(3,4-Dimethylphenyl)pyrazolo[1,5-c]pyridin-5-yl]-N-methylbenzamide 3-[2-(4-Cyanophenyl)pyrazolo[1,5-a]pyridin-5-yl]-N-methylbenzamide 3-[2-(2,3-Difluorophenyl)pyrazolo[1,5-a]pyridin-5-yl]-N-methylbenzamide N-Methyl-3-(2-o-tolylpyrazolo[1,5-a]pyridin-5-yl)benzamide 3-[3-Chloro-2-(4-fluorophenyl)pyrazolo[1,5-c]pyridin-5-yl]-N-methylbenzamide In accordance with the invention, the compounds of general formula (I) may be prepared according to the process described in Scheme 1.

Scheme 1

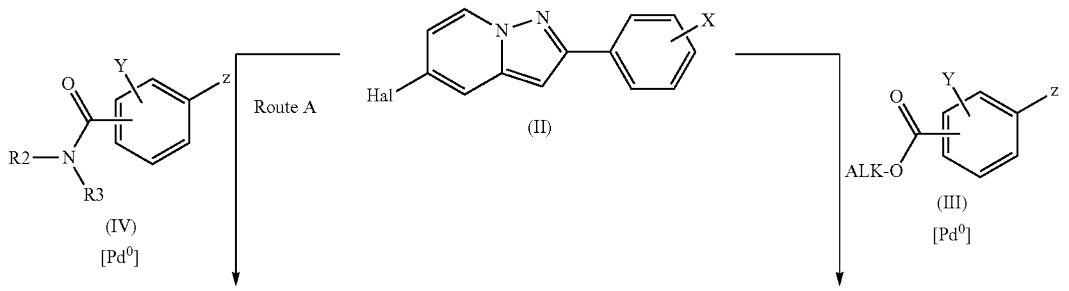

-continued

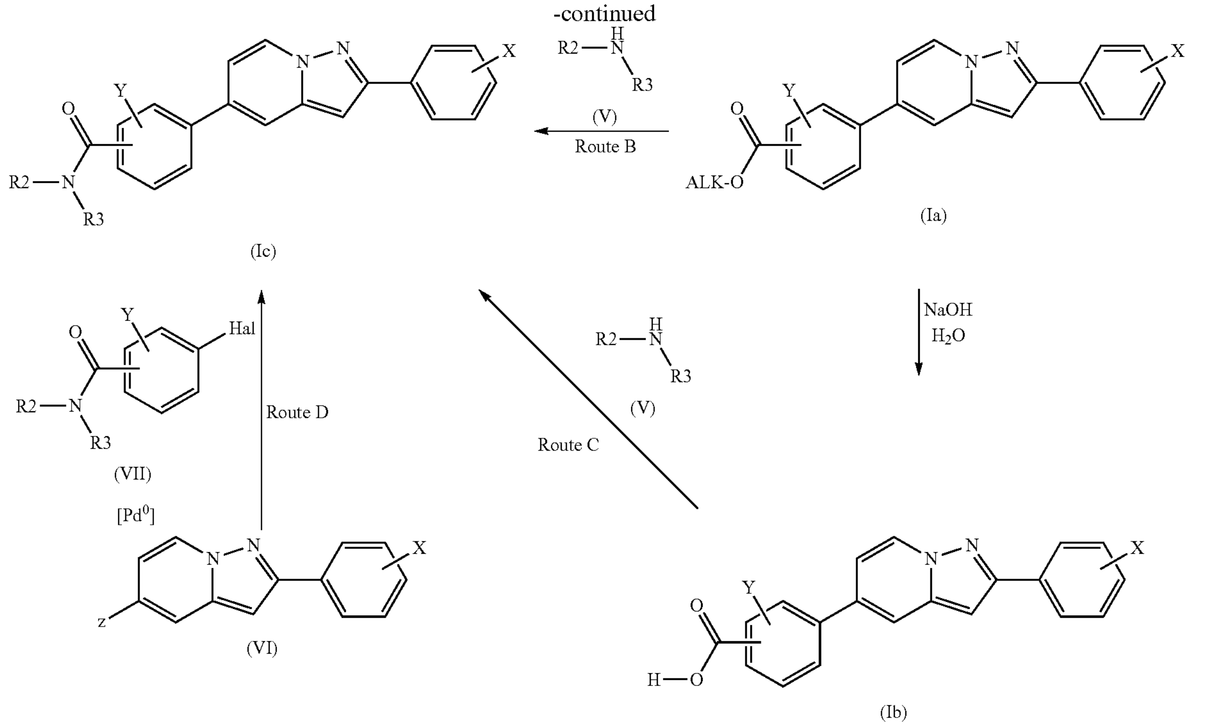

(Ic) (Ia) (VII) (VI) (Ib)

According to Scheme 1, the compounds of general formula (Ia), in which R1 represents OR4, R4 represents an alkyl group ALK, R represents a hydrogen atom, and X and Y are as defined previously, may be prepared via a coupling reaction, catalysed with a metal such as palladium, between a compound of general formula (II) in which R represents a hydrogen atom, X is as defined previously and Hal represents a halogen atom, and a derivative of general formula (III) in which Y and ALK are as defined previously, and Z represents a boron derivative.

According to Scheme 1, the compounds of general formula (Ib), in which R1 represents OR4, R represents a hydrogen atom and X and Y are as defined previously and R4 represents a hydrogen atom, may be prepared via a hydrolysis reaction of the compounds of general formula (Ia) with a base such as sodium hydroxide in an aqueous-alcoholic medium.

According to Scheme 1 route A, the compounds of general formula (Ic) in which R1 represents NR2R3, R represents a hydrogen atom and X, Y, R2 and R3 are as defined previously may be prepared via a coupling reaction, catalysed with a metal such as palladium, between a compound of general formula (II) in which R represents a hydrogen atom, X is as defined previously and Hal represents a halogen atom, and a derivative of general formula (IV) in which Y, R2 and R3 are as defined previously and Z represents a boron derivative.

According to Scheme 1 route B, the compounds of general formula (Ic), in which R1 represents NR2R3, R represents a hydrogen atom and X, Y, R2 and R3 are as defined previously, may be prepared via a reaction between a compound of general formula (Ia), in which R1 represents OR4, R4 represents an alkyl group ALK, R represents a hydrogen atom and X and Y are as defined previously, and an amine of general fottnula (V) in which R2 and R3 are as defined previously, in the presence of trimethylaluminium in solution or else complexed with a tertiary amine such as DABCO according to the method described by D. Glynn, D. Bernier and S. Woodward in *Tetrahedron Letters,* 2008, 49, 5687-5688.

According to Scheme 1 route C, the compounds of general formula (Ic), in which R1 represents NR2R3, R represents a hydrogen atom and X, Y, R2 and R3 are as defined previously, may be prepared via a reaction between a compound of general formula (Ib), in which R1 represents OR4, R represents a hydrogen atom, X and Y are as defined previously and R4 represents a hydrogen atom, and an amine of general formula (V) in which R2 and R3 are as defined previously, in the presence of an acid activator such as isobutyl chloroformate.

According to Scheme 1 route D, the compounds of general formula (Ic), in which R1 represents NR2R3, R represents a hydrogen atom and X, Y, R2 and R3 are as defined previously, may be prepared via a coupling reaction, catalysed with a metal such as palladium, between a compound of general formula (VI) in which R represents a hydrogen atom, X is as defined previously and Z represents a boron derivative, and a derivative of general formula (VII) in which Y, R2 and R3 are as defined previously and Hal represents a halogen atom.

The compounds of general formula (Ic) in which R2 and R3 each represent a hydrogen atom may also be prepared according to the process described in Scheme 2.

Scheme 2

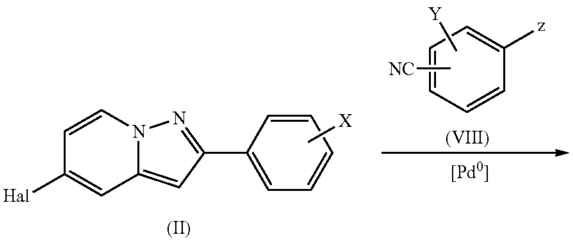

(VIII) (II)

-continued

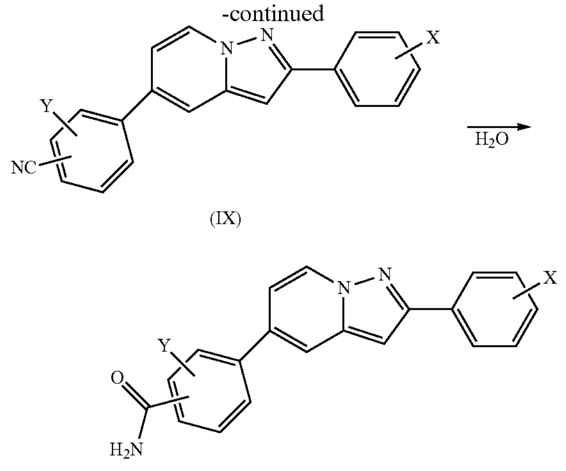

(IX)

(Ic)

In Scheme 2, the compounds of general formula (Ic), in which R1 represents NH2, R represents a hydrogen atom and X and Y are as defined previously, may be obtained via hydrolysis of the nitriles of general formula (IX), for example using hydrogen peroxide in the presence of base. The compounds of general formula (IX) may be obtained via a coupling reaction, catalysed with a metal such as palladium, between a compound of general formula (II) in which R represents a hydrogen atom, X is as defined previously and Hal represents a halogen atom, and a derivative of general formula (VIII) in which Y is as defined previously, CN represents a cyano group and Z represents a boron derivative.

In accordance with the invention, the compounds of general formula (I) may be prepared according to the process described in Scheme 3.

Scheme 3

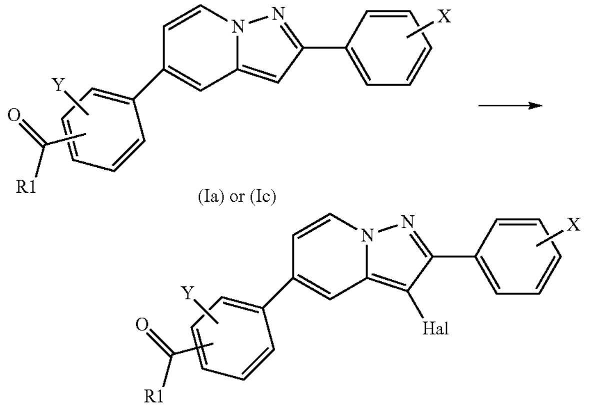

(Ia) or (Ic)

(Id)

According to Scheme 3, the compounds of general formula (Id), in which X, Y and R1 are as defined previously and R represents a halogen atom Hal, may be prepared via electrophilic halogenation of compound (Ia) or (Ic), for example via chlorination, using an agent such as N-chlorosuccinimide In accordance with the invention, the compounds of general formula (II) and (VI) may be prepared according to the process described in Scheme 4.

Scheme 4

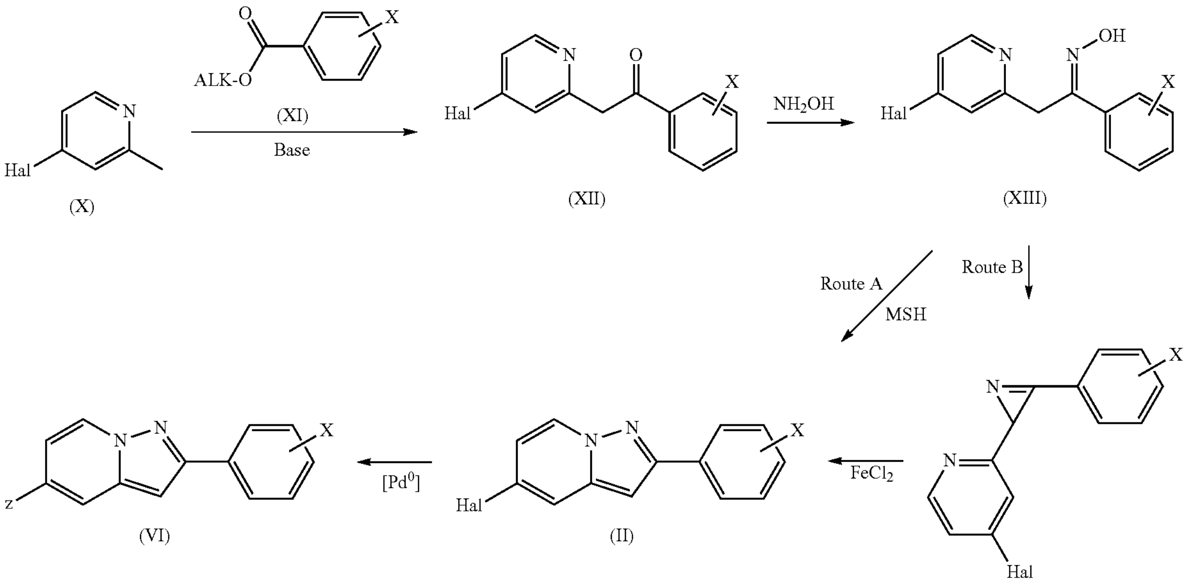

(X)

(XII)

(XIII)

(XIV)

(II)

(VI)

In Scheme 4 route A, the compounds of general formula (II), in which X is as defined previously, R represents a hydrogen atom and Hal represents a halogen atom, may be prepared via the action of O-(mesitylenesulfonyl)hydroxylamine (MSH) on a compound of general formula (XIII) in which X and Hal are as defined previously, for example according to the method described by Y. Tamura, J.-H. Kim, Y. Miki, H. Hayashi, M. Ikeda, in *J. Het. Chem.*, 1975, 12, 481.

In Scheme 4 route B, the compounds of general formula (II), in which X is as defined previously, R represents a hydrogen atom and Hal represents a halogen atom, may also be prepared via conversion of the compounds of general formula (XIII) into compounds of general formula (XIV) in which X and Hal are as defined previously, via the action of an acid anhydride such as trifluoroacetic anhydride in the presence of a base such as triethylamine, followed by cyclization to compounds of general formula (II) in the presence of a catalyst such as ferrous chloride, for example according to the method described by K. S. Gudmundsson in *Bioorg. Med. Chem.*, 2005, 13, 5346.

Compounds (XIII) may be obtained from compounds (XII) via the action of hydroxylamine Compounds (XII) may be obtained from the picolines of general formula (X) and from the esters of general formula (XI) in which X is as defined previously and ALK represents an alkyl group, in the presence of a strong base, for example according to the method described by K. S. Gudmundsson in *Bioorg. Med. Chem.*, 2005, 13, 5346.

Finally, compounds (VI) in which Z represents a boron derivative may be prepared according to Scheme 3 via a coupling reaction, for example of bis(pinacolato)diboron, on compounds (II), catalysed with a metal such as palladium according to the method described by E. F. DiMauro and R. Vitullo in *J. Org. Chem.*, 2006, 71(10), 3959.

In Schemes 1, 2, 3 and 4, the starting compounds and the reagents, when their preparation method is not described, are commercially available or described in the literature, or alternatively may be prepared according to methods that are described therein or that are known to those skilled in the art.

According to another of its aspects, a subject of the invention is also the compound of formula (VI-1). This compound is useful as an intermediate in the synthesis of the compounds of formula (I).

(VI-1)

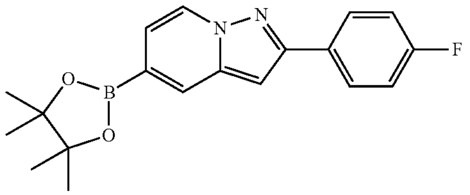

The examples that follow describe the preparation of certain compounds in accordance with the invention. These examples are not limiting, and serve merely to illustrate the present invention. The numbers of the compounds given as examples refer to those given in the table hereinbelow, which illustrates the chemical structures and physical properties of a number of compounds according to the invention.

EXAMPLE 1

Methyl 3-[2-(4-chlorophenyl)pyrazolo[1,5-a]pyridin-5-yl]benzoate

Compound 1 of the Table

1.1 2-(4-Bromopyridin-2-yl)-1-(4-chlorophenyl) ethanone

Under a stream of nitrogen, 5 g (29.07 mmol) of 4-bromo-2-methylpyridine and 11.27 g (61.04 mmol) of ethyl 4-chlorobenzoate are placed in a round-bottomed flask and dissolved in 50 mL of anhydrous tetrahydrofuran. The solution is cooled to 5° C. and 70 mL (70 mmol) of a lithium hexamethyldisilazane solution (1M in tetrahydrofuran) are added dropwise. After addition, the mixture is stirred at room temperature for 2 hours, cooled to 5° C., and 100 mL of water are then gradually added. The medium is then diluted with 250 mL of ethyl acetate and 100 mL of water. The organic phase is separated out and the aqueous phase is extracted twice with 100 mL of ethyl acetate. The organic phases are then combined, dried over sodium sulfate and filtered. 15 g of silica are then added to the filtrate, which is then concentrated under reduced pressure. The powder obtained is used as solid deposit for a chromatography on silica gel, eluting with a mixture of cyclohexane and ethyl acetate (9/1). 8.4 g (93%) of compound are obtained in the faun of a yellow powder.

LC-MS: M+H=310

$^1$H NMR (DMSO) δ (ppm): 4.6 (s, 2H); 6.4 (s, 1H); 7.4 (s, 1H); from 7.5 to 7.6 (m, 6H); 7.7 (s, 1H); 7.9 (d, 2H); 8.1 (d, 2H); 8.3 (d, 1H); 8.4 (d, 1H); 15.0 (s, 1H) (ketone/enol mixture: 40/60).

1.2 2-(4-Bromopyridin-2-yl)-1-(4-chlorophenyl) ethanone Oxime 8.4 g (27.05 mmol) of 2-(4-bromopyridin-2-yl)-1-(4-chlorophenyl)ethanone are placed in 150 mL of ethanol in a round-bottomed flask. 22 mL (272.56 mmol) of pyridine and 7.5 g (107.93 mmol) of hydroxylamine monohydrochloride are added. The mixture is then stirred for 5 hours at room temperature, and the reaction medium is then concentrated under reduced pressure until a pasty yellow solid is obtained, which is taken up in 400 mL of ethyl acetate and 400 mL of water. The organic phase is separated out and the aqueous phase is extracted three times with 200 mL of ethyl acetate. The organic phases are then combined, dried over sodium sulfate and filtered. The filtrate is concentrated under reduced pressure: 8.1 g (91.9%) of compound are obtained in the form of a blue powder.

LC-MS: M+H=325

$^1$H NMR (DMSO) δ (ppm): 4.3 (s, 2H); 7.45 (m, 2H); 7.50 (d, 1H); 7.55 (s, 1H); 7.75 (m, 2H); 8.35 (d, 1H); 11.65 (s, 1H).

1.3. 5-Bromo-2-(4-chlorophenyl)pyrazolo[1,5-a]pyridine 12.9 g (45.21 mmol) of ethyl O-(2-mesitylenesulfonyl) acetohydroxamate are placed in 30 mL of 1,4-dioxane in a round-bottomed flask. The solution is cooled to 0° C. and 13.5 mL (156.60 mmol) of perchloric acid (70% in water) are added. 10 mL of 1,4-dioxane are then added and the medium is stirred vigorously for 2 hours 30 minutes at 0° C. The medium is then poured into 350 mL of ice-cold water. The medium is left at about 0° C. for 10 minutes, and the white solid formed is then recovered by filtration on a sinter funnel (do not dry completely, since the product is potentially explosive in dry fowl). The pasty white solid obtained is washed with 350 mL of ice-cold water and then taken up in 250 mL of 1,2-dichloroethane and 150 mL of brine cooled to about 5° C. The organic phase is recovered and filtered through a hydrophobic cartridge. The filtrate is recovered and is added dropwise to a solution, cooled to about 0° C., of 8.1 g (24.88 mmol) of 2-(4-bromopyridin-2-yl)-1-(4-chlorophenyl)ethanone oxime (compound obtained in step 1.2) in 150 mL of 1,2-dichloroethane After addition, the mixture is allowed to warm to room temperature and is stirred for 3 hours. 250 mL of dichloromethane, 200 mL of water and 100 mL of aqueous NaOH solution (1N) are then successively added to the medium. The resulting mixture is stirred and the phases are then allowed to separate by settling. The organic phase is separated out and the aqueous phase is extracted with twice 200 mL of dichloromethane. The organic phases are then combined, filtered on a hydrophobic cartridge (Radleys® 70 mL liquid/liquid extraction column) and then mixed with 15 g of silica. The filtrate is then concentrated under reduced pressure. A brown powder is obtained, which is used as solid deposit for a chromatography on silica gel, eluting with a mixture of cyclohexane and dichloromethane (1/1). 5.8 g (75%) of compound are obtained in the form of a slightly yellow fleecy solid.

LC-MS: M+H=307.

$^{1}$H NMR (DMSO) δ (ppm): 7.0 (d, 1H); 7.1 (s, 1H); 7.6 (d, 2H); 8.0 (s, 1H); 8.1 (d, 2H); 8.7 (d, 1H).

1.4 Methyl 3-[2-(4-chlororophenyl)pyrazolo[1,5-a]pyridin-5-yl]benzoate 0.235 g (0.76 mmol) of 5-bromo-2-(4-chlorophenyl)pyrazolo[1,5-a]pyridine obtained in step 1.3, 0.165 g (0.92 mmol) of 3-methoxycarbonylphenylboronic acid, 0.750 g (2.30 mmol) of caesium carbonate and 0.065 g (0.08 mmol) of [1,1'-bis(diphenylphosphino)-ferrocene]dichloropalladium (II) are placed in a round-bottomed flask in the presence of 5 mL of a THF-water mixture (9/1). The medium is then maintained at 70° C. for 1 hour 30 minutes, and is then cooled to room temperature and diluted with 30 mL of dichloromethane and 30 mL of water. The two-phase medium is filtered on a hydrophobic cartridge (Radleys® 70 mL liquid/liquid extraction column) and the filtrate is then concentrated under reduced pressure: the residue obtained is chromatographed on silica gel, eluting with a mixture of cyclohexane and ethyl acetate (8/2). 0.200 g (72%) of expected compound is obtained in the fottu of a beige powder.

Melting point (° C.): 180-182

LC-MS: M+H=363

$^{1}$H NMR (DMSO) δ (ppm): 3.95 (s, 3H); 7.20 (s, 1H); 7.35 (d, 1H); 7.60 (d, 2H); 7.70 (t, 1H); from 8.00 to 8.20 (m, 5H); 8.35 (s, 1H); 8.85 (d, 1H).

EXAMPLE 2

3-[2-(4-Chlorophenyl)pyrazolo[1,5-a]pyridin-5-yl]benzamide

Compound 2 of the Table 2.1 3-[2-(4-Chlorophenyl)pyrazolo[1,5-a]pyridin-5-yl]benzonitrile 0.850 g (2.76 mmol) of 5-bromo-2-(4-chlorophenyl)pyrazolo[1,5-a]pyridine obtained according to the protocol of step 1.3 is placed in a round-bottomed flask with 0.490 g (3.33 mmol) of 3-cyanophenylboronic acid, 2.70 g (8.29 mmol) of caesium carbonate and 0.225 g (0.26 mmol) of [1,1'-bis(diphenylphosphino)ferrocene]clichloropalladium (II) in the presence of 20 mL of a THF-water mixture (9/1). The medium is then maintained at 75° C. for 3 hours, followed by addition of a further 0.245 g (1.66 mmol) of 3-cyanophenylboronic acid, 1.35 g (4.14 mmol) of caesium carbonate and 0.115 g (0.14 mmol) of [1,1'-bis(diphenylphosphino)ferrocene]dichloropalladium (II) and the medium is stirred at 75° C. for 1 hour 30 minutes. The medium is then diluted with 100 mL of ethyl acetate and 100 mL of water. The organic phase is then recovered and the aqueous phase is extracted twice with 100 mL of ethyl acetate. The organic phases are then combined, dried over sodium sulfate and filtered. The filtrate is then concentrated under reduced pressure and the residue obtained is dissolved in tetrahydrofuran and concentrated under reduced pressure, after by addition of 10 g of silica. The residue is chromatographed on silica gel, eluting with a mixture of cyclohexane and ethyl acetate (8/2). 0.185 g (20.2%) of expected compound is obtained in the form of a white powder.

LC-MS: M+H=330

$^{1}$H NMR (DMSO) δ (ppm): 7.19 (s, 1H); 7.37 (dd, 1H); 7.56 (m, 2H); 7.74 (t, 1H); 7.90 (m, 1H); 8.06 (m, 21-1); from 8.15 to 8.24 (m, 21-1); 8.35 (m, 1H); 8.82 (d, 1H).

2.2 3-[2-(4-Chlorophenyl)pyrazolo[1,5-a]pyridin-5-yl]benzamide 0.150 g (0.45 mmol) of [2-(4-chlorophenyl)pyrazolo[1,5-c]pyridin-5-yl]benzonitrile obtained in step 2.1 is placed in a round-bottomed flask with 5 mL of anhydrous dimethyl sulfoxide. The medium is then cooled to about 10° C. and 0.100 mL (1.17 mmol) of aqueous hydrogen peroxide solution (35% in water) and 0.035 g (0.25 mmol) of potassium carbonate are added. The medium is gradually warmed to room temperature and stirred for 1 hour. The medium is then cooled to about 5° C. and 0.500 mL (5.85 mmol) of hydrogen peroxide and 0.250 g (1.78 mmol) of potassium carbonate are added. The medium is then stirred for 1 hour 30 minutes at room temperature, followed by dilution in 50 mL of water. The medium is filtered through a sinter funnel, and a powder is recovered, which is chromatographed (by solid deposition) on silica gel, eluting with a mixture of dichloro-methane and methanol (9/1). 0.090 g (56.8%) of expected compound is obtained in the form of a white powder.

Melting point (° C.): 283-285

LC-MS: M+H=348

$^{1}$H NMR (DMSO) δ (ppm): 7.17 (s, 1H); 7.36 (dd, 1H); 7.47 (s, 1H); 7.56 (m, 2H); 7.61 (t, 1H); 7.94 (m, 1H); 8.00 (m, 1H); 8.07 (m, 2H); 8.11 (m, 1H); 8.15 (s, 1H); 8.32 (m, 1H); 8.82 (d, 1H).

EXAMPLE 3

3-[2-(4-Chlorophenyl)pyrazolo[1,5-a]pyridin-5-yl]-N,N-dimethyl-benzamide

Compound 3 of the Table

Under a stream of nitrogen, 0.900 mL (1.80 mmol) of a dimethylamine solution (2M in tetrahydrofuran) and 8 mL of toluene are placed in a round-bottomed flask. The medium is then cooled to about 0° C. and 0.900 mL (1.80 mmol) of a trimethylaluminium solution (2M in toluene) is then added dropwise. After the addition, the medium is stirred at about 0° C. for 25 minutes, followed by addition of 0.200 g (0.55 mmol) of methyl 3-[2-(4-chlororophenyl)-pyrazolo[1,5-a]pyridin-5-yl]benzoate obtained in step 2.1. The medium is then maintained at 90° C. for 3 hours, followed by cooling to about 0° C. The medium is then hydrolysed by dropwise addition of 10 mL of hydrochloric acid solution (1N). After the addition, the medium is warmed to room temperature and then diluted with 60 mL of dichloromethane and 60 mL of water. The pH of the aqueous phase is brought to about 11 with sodium hydroxide solution (1N) and the two-phase medium obtained is then filtered on a sinter funnel packed with Celite. The filtrate is recovered and passed through a hydrophobic cartridge (Radleys® 70 mL liquid/liquid extraction column). The filtrate is recovered and concentrated under reduced pressure after addition of 1.2 g of silica. The residue obtained is chromatographed on silica gel, eluting with a mixture of cyclohexane and ethyl acetate (3/7).

0.121 g (58.4%) of expected compound is obtained in the thin, of a white powder.

Melting point (° C.): 175-177

LC-MS: M+H=376

$^1$H NMR (DMSO) δ (ppm): 3.02 (d, 6H); 7.15 (s, 1H); 7.35 (dd, 1H); 7.46 (m, 1H); from 7.50 to 7.67 (m, 3H); 7.85 (m, 1H); 7.91 (m, 1H); from 8.00 to 8.15 (m, 3H); 8.80 (d, 1H).

EXAMPLE 4

3-[2-(4-Chlorophenyl)pyrazolo[1,5-a]pyridin-5-yl]-N-methylbenzamide

Compound 4 of the Table

The process is performed according to the procedure described in Example 3, starting with 0.200 g (0.55 mmol) of methyl 3-[2-(4-chlororophenyl)pyrazolo[1,5-a]pyridin-5-yl] benzoate obtained in step 3.1, 0.900 mL (1.80 mmol) of a methylamine solution (2M in tetrahydro-furan) and 0.900 mL (1.80 mmol) of a trimethylaluminium solution (2M in toluene) in 8 mL of toluene. After chromatography on silica gel, eluting with a mixture of cyclohexane and ethyl acetate (1/1), 0.151 g (75.6%) of expected compound is obtained in the form of a white powder.

Melting point (° C.): 234-236

LC-MS: M+H=362

$^1$H NMR (DMSO) δ (ppm): 2.85 (d, 3H); 7.18 (s, 1H); 7.35 (m, 1H); from 7.51 to 7.68 (m, 3H); 7.90 (m, 1H); 8.00 (m, 1H); from 8.02 to 8.12 (m, 3H); 8.28 (m, 1H); 8.62 (m, 1H); 8.82 (d, 1H).

EXAMPLE 5

Methyl 3-[2-(4-fluorophenyl)pyrazolo[1,5-a]pyridin-5-yl]benzoate

Compound 5 of the Table 5.1 2-(4-bromopyridin-2-yl)-1-(4-fluorophenyl)ethanone

Under a stream of nitrogen, 5.0 g (29.07 mmol) of 4-bromo-2-picoline and 10.2 g (60.95 mmol) of ethyl 4-fluorobenzoate are placed in a round-bottomed flask and dissolved in 50 mL of anhydrous tetrahydrofuran. The mixture is cooled to 0° C. and 70 mL (70 mmol) of a lithium hexamethyldisilazane solution (1M in tetrahydrofuran) are added dropwise. After addition, the mixture is stirred at room temperature for 2 hours, cooled to 5° C., and 100 mL of water are then gradually added. The medium is then diluted with 250 mL of ethyl acetate and 100 mL of water. The organic phase is separated out and the aqueous phase is extracted twice with 100 mL of ethyl acetate. The organic phases are then combined, dried over sodium sulfate and filtered. 15 g of silica are then added to the filtrate, and the resulting mixture is stirred and then concentrated under reduced pressure. The powder obtained is used as a solid deposit for a chromatography on silica gel, eluting with a mixture of cyclohexane and ethyl acetate (9/1). 7.5 g (88%) of compound are obtained in the form of a yellow powder.

LC-MS: M+H=294 (ketone/enol ratio: 43/57)

$^1$H NMR (DMSO) δ (ppm): 4.56 (s, 2H); 6.34 (s, 1H); from 7.23 to 7.40 (m, 5H); 7.53 (d, 1H); 7.56 (m, 1H); 7.70 (d, 1H); from 7.81 to 7.92 (m, 2H); from 8.04 to 8.16 (m, 2H); 8.29 (d, 1H); 8.37 (d, 1H); 15.0 (s, 1H).

5.2 2-(4-bromopyridin-2-yl)-1-(4-fluorophenyl)ethanone Oxime 7.5 g (24.26 mmol) of 2-(4-bromopyridin-2-yl)-1-(4-fluorophenyl)ethanone are placed in a round-bottomed flask containing 100 mL of absolute ethanol. 20 mL (247.78 mmol) of pyridine and 7.08 g (101.88 mmol) of hydroxylamine monohydrochloride are added, and the medium is then stirred for 3 hours at room temperature. The ethanol is then evaporated off under vacuum and the residue obtained is taken up in 250 mL of water and 250 mL of ethyl acetate. The organic phase is separated out and the aqueous phase is then extracted 5 times with 150 mL of ethyl acetate. The organic phases are then combined, dried over sodium sulfate and concentrated under vacuum. 7.82 g of compound are obtained.

LC-MS: M+H=309

$^1$H NMR (DMSO-$d_6$, δ in ppm): 4.26 (s, 2H); 7.19 (t, 2H); 7.50 (m, 2H); 7.75 (m, 2H); 8.33 (d, 1H); 11.50 (s, 1H) (production of the oxime (E)).

5.3 5-bromo-2-(4-fluorophenyl)pyrazolo[1,5-a]pyridine 7.82 g (25.50 mmol) of 2-(4-bromopyridin-2-yl)-1-(4-fluorophenyl)ethanone oxime are placed in a round-bottomed flask and dissolved in 400 mL of 1,2-dichloroethane. An O-(mesitylenesulfonyl)hydroxylamine solution (0.27 M in 1,2-dichloroethane—compound obtained according to the protocol described in step 1.3) is added dropwise to the medium cooled to about 0° C. After the addition, the medium is stirred at room temperature for 1 hour 30 minutes. The medium is then diluted with 200 mL of water and 200 mL of sodium hydroxide solution (1N). The two-phase medium is stirred and the phases are then separated by settling. The organic phase is separated out and the aqueous phase is then extracted 4 times with 200 mL of dichloromethane. The organic phases are then combined, dried over sodium sulfate and filtered. 15 g of silica are then added to the filtrate, and the resulting mixture is then concentrated under reduced pressure. The powder obtained is used as solid deposit for a chromatography on silica gel, eluting with a mixture of cyclohexane and dichloromethane (1/1). 5.06 g (68%) of compound are obtained in the form of a fleecy white powder.

LC-MS: M+H=291

$^1$H NMR (DMSO-$d_6$, δ in ppm): from 7.00 to 7.10 (m, 2H); 7.45 (m, 2H); 8.05 (m, 3H); 8.70 (d, 1H).

5.4 methyl 3-[2-(4-fluorophenyl)pyrazolo[1,5-a]pyridin-5-yl]benzoate

Under a stream of nitrogen, 0.400 g (1.37 mmol) of 5-bromo-2-(4-fluorophenyl)pyrazolo[1,5-a]pyridine obtained in step 5.3, 0.300 g (1.67 mmol) of 3-methoxycarbonylphenylboronic acid and 1.330 g (4.08 mmol) of caesium carbonate are placed in 5 mL of a 9/1 mixture of tetrahydrofuran and water. 0.11 g (0.13 mmol) of [1,1'-bis(diphenylphosphino)ferrocene]dichloropalladium (II) is added and the medium is heated at 70° C. for 4 hours. The medium is then cooled to room temperature and diluted with 40 mL of dichloromethane and 40 mL of water. The medium is then filtered on a hydrophobic cartridge (Radleys® 70 mL liquid/ liquid extraction column) and the organic phase is recovered and concentrated under reduced pressure after addition of 2 g of silica. The residue is purified by chromatography on silica gel, eluting with a mixture of cyclohexane and ethyl acetate (9/1). 0.340 g (71%) of expected product is obtained in the form of a white powder.

Melting point (° C.): 162-164

LC-MS: M+H=347

$^1$H NMR (DMSO) δ (ppm): 3.95 (s, 3H); 7.15 (s, 1H); from 7.30 to 7.38 (m, 3H); 7.70 (t, 1H); from 8.00 to 8.15 (m, 5H); 8.35 (m, 1H); 8.80 (d, 1H).

EXAMPLE 6

3-[2-(4-Fluorophenyl)pyrazolo[1,5-a]pyridin-5-yl]-N-methylbenzamide

Compound 6 of the Table

The process is performed according to the procedure described in Example 3, starting with 0.200 g (0.58 mmol) of methyl 3-[2-(4-fluorophenyl)pyrazolo[1,5-c]pyridin-5-yl]benzoate obtained in step 7.4, 1.00 mL (2.00 mmol) of a methylamine solution (2M in tetrahydro-furan) and 1.00 mL (2.00 mmol) of a trimethylaluminium solution (2M in toluene) in 8 mL of toluene. After chromatography on silica gel, eluting with a mixture of cyclohexane and ethyl acetate (1/1), 0.235 g (67.7%) of expected compound is recovered in the form of a white powder.

Melting point (° C.): 214-216

LC-MS: M+H=346

$^1$H NMR (DMSO) δ (ppm): 2.85 (d, 3H); 7.15 (s, 1H); from 7.26 to 7.46 (m, 3H); 7.62 (m, 1H); 7.90 (m, 1H); 8.00 (m, 1H); from 8.05 to 8.21 (m, 3H); 8.29 (m, 1H); 8.60 (m, 1H); 8.82 (d, 1H).

EXAMPLE 7

3-[2-(4-Fluorophenyl)pyrazolo[1,5-a]pyridin-5-yl]-2,N-dimethylbenzamide

Compound 10 of the Table 7.1 2-(4-Fluorophenyl)-5-(4,4,5,5-tetramethyl-[1,3,2]dioxaborolan-2-yl)pyrazolo[1,5-a]pyridine Compound VI-1

1.00 g (3.43 mmol) of 5-bromo-2-(4-fluorophenyl)pyrazolo[1,5-c]pyridine obtained as in step 7.3 is placed in contact with 1.05 g (4.13 mmol) of bis(pinacolato)diboron, 1.00 g (10.19 mmol) of potassium acetate and 0.280 g (0.34 mmol) of [1,1'-bis(diphenyl-phosphino)ferrocene]dichloropalladium (II) in 14 mL of dioxane.

The medium obtained is irradiated by microwave at 140° C. for 20 minutes and then diluted with 100 mL of dichloromethane and 100 mL of water. The two-phase medium is then filtered through a hydrophobic cartridge (Radleys® 70 mL liquid/liquid extraction column). The organic phase is recovered and concentrated under reduced pressure, after adding 4 g of silica. The residue obtained is chromatographed on silica gel, eluting with a mixture of cyclohexane and ethyl acetate (9/1).

0.992 g (85.4%) of expected compound is obtained in the form of a pink powder.

LC-MS: M+H=338 (degradation on the column to boronic acid M+H=257)

$^1$H NMR (DMSO) δ (ppm): 1.35 (s, 12H); 7.00 (m, 1H); 7.19 (s, 1H); 7.34 (t, 2H); 8.05 (m, 3H); 8.69 (d, 1H).

7.2 3-Bromo-2,N-dimethylbenzamide 0.500 g (2.33 mmol) of 3-bromo-2-methylbenzoic acid is placed in a round-bottomed flask in the presence of 1.51 mL (10.83 mmol) of triethylamine, 0.408 g (3.02 mmol) of N-hydroxybenzotriazole monohydrate, 0.579 g (3.02 mmol) of 1-(3-dimethylaminopropyl)-3-ethylcarbodiimide monohydrochloride and 5 mL of dichloromethane. The medium is stirred at room temperature for 1 hour, followed by addition of 1.51 mL (3.02 mmol) of a methylamine solution (2M in tetrahydrofuran). The medium is stirred overnight at room temperature, followed by addition of a further 0.5 mL (1 mmol) of methylamine solution, and the mixture is stirred overnight. The medium is then concentrated under reduced pressure, and 5 mL of dichloromethane and 0.390 mL (2.99 mmol) of isobutyl chloroformate are added. The medium is again stirred overnight, followed by dilution with 7 mL of dichloromethane and 7 mL of water. The medium is then filtered on a hydrophobic cartridge (Radleys® 70 mL liquid/liquid extraction column). The organic phase is recovered and concentrated under reduced pressure.

0.298 g (56.2%) of expected compound is obtained in the form of a white powder.

LC-MS: M+H=228

$^1$H NMR (DMSO) δ (ppm): 2.31 (s, 3H); 2.80 (d, 3H); from 7.05 to 7.35 (m, 2H); 7.68 (m, 1H); 8.32 (bs, 1H).

7.3 3-[2-(4-Fluorophenyl)pyrazolo[1,5-a]pyridin-5-yl]-4,N-dimethylbenzamide 0.150 g (0.44 mmol) of 2-(4-fluorophenyl)-5-(4,4,5,5-tetramethyl-[1,3,2]dioxaborolan-2-yl)pyrazolo[1,5-a]pyridine obtained in step 7.1 and 0.144 g (0.63 mmol) of 3-bromo-2-N-dimethylbenzamide obtained in step 10.2 are placed in contact with 0.434 g (1.33 mmol) of caesium carbonate and 0.036 g (0.044 mmol) of [1,1'-bis(diphenylphosphino)-ferrocene]dichloropalladium (II) in 5 mL of a 9/1 mixture of tetrahydrofuran and water. The medium is stirred at 60° C. overnight. The medium is then diluted with 50 mL of dichloromethane and 50 mL of water. The two-phase medium is then filtered on a hydrophobic cartridge (Radleys® 70 mL liquid/liquid extraction column). The organic phase is recovered and concentrated under reduced pressure, after adding 1.5 g of silica. The residue obtained is chromatographed on silica gel, eluting with a mixture of cyclohexane and ethyl acetate (1/1).

0.103 g (65%) of expected compound is obtained in the form of a white powder.

Melting point (° C.): 240-242

LC-MS: M+H=360

$^1$H NMR (DMSO) δ (ppm): 2.37 (s, 3H); 2.80 (d, 3H); 6.86 (d, 1H); 7.10 (s, 1H); from 7.33 to 7.44 (m, 5H); 7.63 (s, 1H); 8.10 (m, 2H); 8.28 (s, 1H); 8.76 (d, 1H).

EXAMPLE 8

N-Cyclopropyl-3-[2-(4-fluorophenyl)pyrazolo[1,5-a]pyridin-5-yl]-benzamide

Compound 15 of the Table 0.0382 g (0.67 mmol) of cyclopropylamine is diluted with 10 mL of anhydrous tetrahydro-furan. 0.0859 g (0.33 mmol) of DABAL (double adduct of trimethylaluminium with 1,4- diazabicyclo[2.2.2]octane) is then gradually added, and the medium is then stirred for 1 hour. 0.145 g (0.42 mmol) of methyl 3-[2-(4-fluorophenyl)pyrazolo[1,5-c]pyridin-5-yl]-benzoate obtained according to protocol 5.4 is then added, and the reaction medium is then irradiated in a microwave oven for twice 30 minutes at 130° C. The medium is then hydrolysed at about 5° C. using 5 mL of water and 5 mL of aqueous hydrochloric acid solution (1N). After the hydrolysis, the medium is diluted with 50 mL of water and 50 mL of dichloromethane, and then filtered through a hydrophobic cartridge (Radleys® 70 mL liquid/liquid extraction column) The organic phase is recovered and concentrated under reduced pressure, after adding 1.5 g of silica. The residue obtained is chromatographed on silica gel, eluting with a mixture of cyclohexane and ethyl acetate (6/4).

0.112 g (72.3%) of expected compound is obtained in the form of a white powder.

Melting point (° C.): 179-181

LC-MS: M+H=372

$^{1}$H NMR (DMSO) δ (ppm): from 0.60 to 0.80 (m, 4H); 3.92 (m, 1H); 7.15 (s, 1H); from 7.30 to 7.39 (m, 3H); 7.61 (t, 1H); 7.88 (d, 1H); 7.98 (d, 1H); 8.10 (m, 3H); 8.22 (s, 1H); 8.57 (m, 1H); 8.81 (d, 1H).

EXAMPLE 9

{3-[2-(4-Fluorophenyl)pyrazolo[1,5-a]pyridin-5-yl]phenyl}-(3-hydroxy-pyrrolidin-1-yl)methanone Compound 22 of the Table 0.100 g (0.30 mmol) of 3-[2-(4-fluorophenyl)pyrazolo[1,5-a]pyridin-5-yl]benzoic acid prepared as in Example 8 is placed in a round-bottomed flask in the presence of 0.170 mL (1.20 mmol) of triethylamine and 20 mL of dichloromethane. 0.051 μL (0.39 mmol) of isobutyl chloroformate is then added and the medium is stirred at room temperature for 2 hours. 0.0341 g (0.39 mmol) of 3-hydroxypyrrolidine is added to the medium, which is stirred for a further 2 hours at room temperature. The medium is then diluted with 50 mL of water and 50 mL of dichloromethane. The two-phase medium is then filtered through a hydrophobic cartridge (Radleys® 70 mL liquid/liquid extraction column). The organic phase is recovered and concentrated under reduced pressure after adding 1 g of silica. The residue obtained is chromatographed on silica gel, eluting with a mixture of cyclohexane and ethyl acetate (6/4).

0.063 g (50%) of expected compound is obtained in the faun of a pale yellow wax.

Melting point (° C.): 173-175

LC-MS: M+H=402

$^{1}$H NMR (DMSO) δ (ppm): from 1.65 to 2.05 (m, 2H); from 3.40 to 3.70 (m, 4H); 4.32 (d, 1h); 5.00 (d, 1H); 7.11 (s, 1H); 7.32 (m, 3H); 7.60 (m, 2H); 7.93 (d, 2H); 8.08 (m, 31-1); 8.77 (d, 1H).

EXAMPLE 10

N-Methyl-3-(2-p-tolylpyrazolo[1,5-a]pyridin-5-yl)benzamide

Compound 328 of the Table

10.1 2-(4-Bromopyridin-2-yl)-1-p-tolylethanone

Under a stream of nitrogen, 1 g (5.81 mmol) of 4-bromo-2-methylpyridine and 1.75 g (11.60 mmol) of methyl 4-methylbenzoate are placed in a round-bottomed flask and dissolved in 30 mL of anhydrous tetrahydrofuran. The solution is cooled to 5° C. and 14 mL (14 mmol) of a lithium hexamethyldisilazane solution (1M in tetrahydrofuran) are added dropwise. After addition, the mixture is stirred at room temperature for 2 hours 30 minutes and then cooled to 5° C., followed by gradual addition of 20 mL of water. The medium is then diluted with 200 mL of ethyl acetate and 200 mL of water. The organic phase is separated out, dried over sodium sulfate and filtered. 5 g of silica are then added to the filtrate, which is then concentrated under reduced pressure. The powder obtained is used as a solid deposit for a chromatography on silica gel, eluting with a mixture of cyclohexane and ethyl acetate (95/5) to give 1.03 g (61%) of compound in the form of a yellow powder.

LC-MS: M+H=290

10.2 4-Bromo-2-(3-p-tolyl-2H-azirin-2-yl)pyridine 1.03 g of 2-(4-bromopyridin-2-yl)-1-p-tolylethanone obtained in step 13.1 are placed in a round-bottomed flask with 0.99 g (14.2 mmol) of hydroxylamine monohydrochloride, 3 mL (37 mmol) of pyridine and 100 mL of ethanol. The reaction medium is stirred overnight and then concentrated under reduced pressure. The residue obtained is then taken up in 200 mL of ethyl acetate and 200 mL of water. The organic phase is recovered, dried over sodium sulfate and then concentrated under reduced pressure. 1.10 g of compound are recovered and dissolved in a round-bottomed flask containing 0 660 mL (4.74 mmol) of triethylamine and 30 mL of dichloromethane. The reaction medium is then cooled to about 5° C. and 0.200 mL (1.42 mmol) of trifluoroacetic anhydride is added dropwise. The medium is then stirred at room temperature for 3 hours, followed by hydrolysis with 100 mL of water. The medium is then stirred for 10 minutes, followed by filtration through a hydrophobic cartridge (Radleys® 70 mL liquid/liquid extraction column). 1.2 g of silica are then added to the filtrate, followed by concentrating under reduced pressure. The powder obtained is used as a solid deposit for a chromatography on silica gel, eluting with a mixture of cyclohexane and ethyl acetate (95/5). 0.746 g (77%) of expected compound is recovered in the form of a white powder.

$^{1}$H NMR (DMSO) δ (ppm): 2.42 (d, 3H); 3.45 (s, 1H); from 7.42 to 7.58 (m, 4H); 7.78 (m, 2H); 8.30 (d, 1H).

10.3 5-Bromo-2-p-tolyl-pyrazolo[1,5-a]pyridine 0.746 g of 4-bromo-2-(3-p-tolyl-2H-azirin-2-yl)pyridine obtained in step 13.2 is dissolved in the presence of 6.6 mg (0.052 mmol) of iron (H) chloride in 30 mL of 1,2-dimethoxyethane. The medium is then refluxed for 6 hours. A further 10 mg (0.078 mmol) of iron (II) chloride are then added and the mixture is refluxed again with stirring for 3 hours. The medium is then diluted with 50 mL of ethyl acetate and 50 mL of water. The organic phase is then recovered, dried over sodium sulfate and filtered. 2 g of silica are then added to the filtrate, followed by concentrating under reduced pressure. The powder obtained is used as a solid deposit for a chromatography on silica gel, eluting with a mixture of cyclohexane and ethyl acetate (85/15). 0.534 g (71%) of expected compound is recovered in the faun of a yellow powder.

LC-MS: M+H=287

$^{1}$H NMR (DMSO) δ (ppm): 2.48 (m, 3H); 7.00 (m, 2H); 7.32 (m, 2H); 7.88 (m, 2H); 8.00 (m, 1H); 8.68 (d, 1H).

10.4 N-methyl-3-(4,4,5,5-tetramethyl-[1,3,2]dioxaborolan-2-yl)benzamide 2.50 g (11.68 mmol) of 3-bromo-N-methylbenzamide, 3.56 g (14.01 mmol) of bis(pinacolato)diboron, 3.43 g (35.04 mmol) of potassium acetate and 0.953 g (1.17 mmol) of [1,1'-bis(diphenylphosphino)ferrocene]dichloropalladium (II) are placed in contact with 20 mL of dioxane and then irradiated by microwave at 130° C. for 45 minutes. The medium is then diluted with 150 mL of ethyl acetate and 100 mL of water. The organic phase is recovered and the aqueous phase is extracted with twice 100 mL of ethyl acetate. The organic phases are then combined, dried over sodium sulfate and then concentrated under reduced pressure, after adding 10 g of silica. The residue obtained is chromatographed on silica gel, eluting with a mixture of cyclohexane and ethyl acetate (8/2).

1.39 g of expected compound are obtained in the form of a pink powder (presence of pinacol).

$^1$HNMR (DMSO) δ (ppm): 1.30 (s, 1H); 2.78 (d, 3H); 7.48 (t, 1H); 7.80 (m, 1H); 7.95 (m, 1H); 8.12 (m, 1H); 8.50 (m, 1H).

10.5 N-Methyl-3-(2-p-tolylpyrazolo[1,5-a]pyridin-5-yl)benzamide 0.150 g (0.52 mmol) of 5-bromo-2-p-tolylpyrazolo[1,5-a]pyridine obtained in step 13.3, 0.136 g (0.52 mmol) of N-methyl-3-(4,4,5,5-tetramethyl-[1,3,2]dioxaborolan-2-yl)benzamide obtained in step 13.4, 0.510 g (1.57 mmol) of caesium carbonate and 0.043 g (0.05 mmol) of [1,1'-bis(diphenylphosphino)ferrocene]dichloropalladium (II) are placed in 5 mL of a 9/1 mixture of tetrahydrofuran and water. The medium is stirred at 65° C. for 4 hours. The medium is then diluted with 50 mL of dichloromethane and 50 mL of water. The two-phase medium is then filtered through a hydrophobic cartridge (Radleys® 70 mL liquid-liquid extraction column). The organic phase is recovered and concentrated under reduced pressure, after adding 1.5 g of silica. The residue obtained is chromatographed on silica gel, eluting with a mixture of cyclohexane and ethyl acetate (1/1).

0.138 g (77.7%) of expected compound is obtained in the form of a beige powder.

Melting point (° C.): 204-206

LC-MS: M+H=342

$^1$H NMR (DMSO) δ (ppm): 2.38 (s, 3H); 2.85 (d, 3H); 7.10 (s, 1H); 7.31 (m, 3H); 7.62 (t, 1H); 7.90 (m, 3H); 7.98 (d, 1H); 8.08 (s, 1H); 8.29 (s, 1H); 8.61 (d, 1H); 8.81 (d, 1H).

EXAMPLE 11

3-[3-Chloro-2-(4-fluorophenyl)pyrazolo[1,5-a]pyridin-5-yl]-N-methyl-benzamide

Compound 34 of the Table 0.100 g (0.29 mmol) of 3-[2-(4-fluorophenyl)pyrazolo[1,5-a]pyridin-5-yl]-N-methyl-benzamide obtained according to protocol 6 is placed in a round-bottomed flask in the presence of 3 mL of dichloromethane. 0.060 g (0.45 mmol) of N-chlorosuccinimide is added, and the medium is then stirred at room temperature overnight. The reaction medium is then diluted with 50 mL of dichloromethane and 50 mL of water. The two-phase medium is then filtered through a hydrophobic cartridge (Radleys® 70 mL liquid/liquid extraction column). The organic phase is recovered and concentrated under reduced pressure, after adding 1.2 g of silica. The residue obtained is chromatographed on silica gel, eluting with a mixture of cyclohexane and ethyl acetate (6/4).

0.0592 g (53.8%) of expected compound is obtained in the faun of a white powder.

Melting point (° C.): 221-223

LC-MS: M+H=380

$^1$H NMR (DMSO) δ (ppm): 2.88 (d, 3H); 7.42 (m, 2H); 7.47 (dd, 1H); 7.64 (t, 1H); 7.93 (m, 1H); 8.01 (m, 1H); 8.05 (m, 1H); 8.10 (m, 2H); 8.31 (m, 1H); 8.63 (m, 1H); 8.88 (d, 1H).

The tables that follow illustrate the chemical structures of general formula (I) (Table 1) and the physicochemical characteristics (Table 2) of a number of examples of compounds according to the invention.

In these tables:

the column "m.p." indicates the melting points of the products in degrees Celsius (° C.);

Me and Et represent, respectively, a methyl group and an ethyl group;

* indicates the bonding atom(s).

TABLE 1

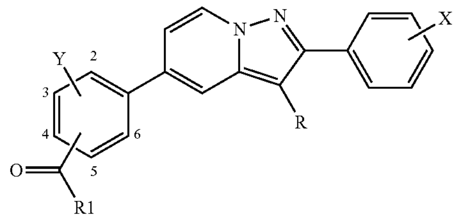

(I)

| No. | R1 | Position (C═O)R1 | X | Y | R |
|---|---|---|---|---|---|
| 1 | OMe | 3 | 4-Cl | H | H |
| 2 | $NH_2$ | 3 | 4-Cl | H | H |
| 3 | $N(Me)_2$ | 3 | 4-Cl | H | H |
| 4 | NHMe | 3 | 4-Cl | H | H |
| 5 | OMe | 3 | 4-F | H | H |
| 6 | NHMe | 3 | 4-F | H | H |
| 7 | 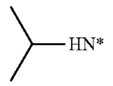 | 3 | 4-F | H | H |
| 8 | $N(Me)_2$ | 3 | 4-F | H | H |
| 9 | 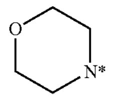 | 3 | 4-F | H | H |
| 10 | NHMe | 3 | 4-F | 2-Me | H |
| 11 | NHMe | 3 | 4-F | 4-Cl | H |
| 12 | NHMe | 3 | 4-F | 6-Cl | H |
| 13 | NHMe | 3 | 4-F | 6-Me | H |
| 14 | NHMe | 4 | 4-F | 3-F | H |
| 15 | 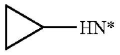 | 3 | 4-F | H | H |
| 16 | 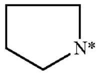 | 3 | 4-F | H | H |
| 17 | NHMe | 3 | 2,6-diF | H | H |
| 18 | NHMe | 3 | 2-F | H | H |
| 19 | NHMe | 3 | $4-CF_3$ | H | H |
| 20 | NHMe | 4 | 4-F | H | H |
| 21 | NHMe | 2 | 4-F | H | H |
| 22 | 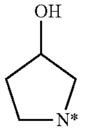 | 3 | 4-F | H | H |

TABLE 1-continued (I)

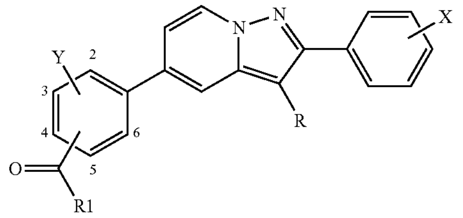

| No. | R1 | Position (C═O)R1 | X | Y | R |
|---|---|---|---|---|---|
| 23 | NHMe | 3 | 2,4-diF | H | H |
| 24 | NHMe | 3 | 4-$OCF_3$ | H | H |
| 25 | NHMe | 3 | 3,4-diF | H | H |
| 26 | NHMe | 3 | 3,5-diF | H | H |
| 27 | NHMe | 3 | 3-F | H | H |
| 28 | NHMe | 3 | 4-Me | H | H |
| 29 | NHMe | 3 | 4-OMe | H | H |
| 30 | NHMe | 3 | 3,4-diMe | H | H |
| 31 | NHMe | 3 | 4-CN | H | H |
| 32 | NHMe | 3 | 2,3-diF | H | H |
| 33 | NHMe | 3 | 2-Me | H | H |
| 34 | NHMe | 3 | 4-F | H | Cl |

TABLE 2

| No. | m.p. ° C. | NMR/[M + H] |
|---|---|---|
| 1 | 180-182 | $^1$H NMR (DMSO) δ (ppm): 3.95 (s, 3H); 7.20 (s, 1H); 7.35 (d, 1H); 7.60 (d, 2H); 7.70 (t, 1H); from 8.00 to 8.20 (m, 5H); 8.35 (s, 1H); 8.85 (d, 1H). M + H = 363 |
| 2 | 283-285 | $^1$H NMR (DMSO) δ (ppm): 7.17 (s, 1H); 7.36 (dd, 1H); 7.47 (s, 1H); 7.56 (m, 2H); 7.61 (t, 1H); 7.94 (m, 1H); 8.00 (m, 1H); 8.07 (m, 2H); 8.11 (m, 1H); 8.15 (s, 1H); 8.32 (m, 1H); 8.82 (d, 1H). M + H = 348 |
| 3 | 175-177 | $^1$H NMR (DMSO) δ (ppm): 3.02 (d, 6H); 7.15 (s, 1H); 7.35 (dd, 1H); 7.46 (m, 1H); from 7.50 to 7.67 (m, 3H); 7.85 (m, 1H); 7.91 (m, 1H); from 8.00 to 8.15 (m, 3H); 8.80 (d, 1H). M + H = 376 |
| 4 | 234-236 | $^1$H NMR (DMSO) δ (ppm): 2.85 (d, 3H); 7.18 (s, 1H); 7.35 (m, 1H); from 7.51 to 7.68 (m, 3H); 7.90 (m, 1H); 8.00 (m, 1H); from 8.02 to 8.12 (m, 3H); 8.28 (m, 1H); 8.62 (m, 1H); 8.82 (d, 1H). M + H = 362 |
| 5 | 162-164 | $^1$H NMR (DMSO) δ (ppm): 3.95 (s, 3H); 7.15 (s, 1H); from 7.30 to 7.38 (m, 3H); 7.70 (t, 1H); from 8.00 to 8.15 (m, 5H); 8.35 (m, 1H); 8.80 (d, 1H). M + H = 347 |
| 6 | 214-216 | $^1$H NMR (DMSO) δ (ppm): 2.85 (d, 3H); 7.15 (s, 1H); from 7.26 to 7.46 (m, 3H); 7.62 (m, 1H); 7.90 (m, 1H); 8.00 (m, 1H); from 8.05 to 8.21 (m, 3H); 8.29 (m, 1H); 8.60 (m, 1H); 8.82 (d, 1H). M + H = 346 |
| 7 | 210-212 | $^1$H NMR (DMSO) δ (ppm): 1.23 (d, 6H); 4.18 (m, 1H); 7.14 (s, 1H); 7.34 (m, 3H); 7.62 (t, 1H); 7.90 (d, 1H); 7.99 (d, 1H); 8.07 (m, 3H); 8.24 (s, 1H); 8.47 (d, 1H); 8.80 (d, 1H). M + H = 374. |
| 8 | 131-133 | $^1$H NMR (DMSO) δ (ppm): 3.03 (d, 6H); 7.12 (s, 1H); from 7.30 to 7.39 (m, 3H); 7.47 (d, 1H); 7.57 (t, 1H); 7.82 (s, 1H); 7.90 (d, 1H); 8.07 (m, 3H); 8.78 (d, 1H). M + H = 360. |
| 9 | 152-154 | $^1$H NMR (DMSO) δ (ppm): from 3.38 to 3.80 (m, 8H); 7.13 (s, 1H); 7.30 to 7.39 (m, 3H); 7.47 (d, 1H); 7.62 (t, 1H); 7.85 (s, 1H); 7.95 (d, 1H); 8.08 (m, 3H); 8.80 (d, 1H). M + H = 402. |
| 10 | 240-242 | $^1$H NMR (DMSO) δ (ppm): 2.37 (s, 3H); 2.80 (d, 3H); 6.86 (d, 1H); 7.10 (s, 1H); from 7.33 to 7.44 (m, 5H); 7.63 (s, 1H); 8.10 (m, 2H); 8.28 (s, 1H); 8.76 (d, 1H). M + H = 360. |
| 11 | 243-245 | $^1$H NMR (DMSO) δ (ppm): 2.83 (d, 3H); 7.12 (s, 1H); from 7.27 to 7.35 (m, 3H); 7.62 (d, 1H); 7.90 (m, 2H); from 8.04 to 8.16 (m, 3H); 8.46 (s, 1H); 8.80 (d, 1H). M + H = 380. |
| 12 | 188-190 | $^1$H NMR (DMSO) δ (ppm): 2.83 (d, 3H); 7.05 (d, 1H); 7.18 (s, 1H); 7.35 (m, 2H); 7.74 (d, 1H); 7.83 (s, 1H); 7.90 (d, 1H); 8.01 (s, 1H); 8.10 (m, 2H); 8.61 (s, 1H); 8.82 (d, 1H). M + H = 380. |
| 13 | 185-187 | $^1$H NMR (DMSO) δ (ppm): 2.49 (s, 3H); 2.83 (d, 3H); 6.97 (d, 1H); 7.10 (s, 1H); 7.35 (m, 2H); 7.46 (d, 1H); 7.70 (s, 1H); 7.83 (m, 2H); 8.08 (m, 2H); 8.47 (s, 1H); 8.77 (d, 1H). M + H = 360. |
| 14 | 227-229 | $^1$H NMR (DMSO) δ (ppm): 2.83 (d, 3H); 7.14 (s, 1H); from 7.30 to 7.39 (m, 3H); from 7.74 to 7.85 (m, 3H); 8.08 (m, 2H); 8.18 (s, 1H); 8.39 (s, 1H); 8.80 (d, 1H). M + H = 364. |
| 15 | 179-181 | $^1$H NMR (DMSO) δ (ppm): from 0.60 to 0.80 (m, 4H); 3.92 (m, 1H); 7.15 (s, 1H); from 7.30 to 7.39 (m, 3H); 7.61 (t, 1H); 7.88 (d, 1H); 7.98 (d, 1H); 8.10 (m, 3H); 8.22 (s, 1H); 8.57 (m, 1H); 8.81 (d, 1H). M + H = 372. |
| 16 | 164-166 | $^1$H NMR (DMSO) δ (ppm): from 1.80 to 2.00 (m, 4H); from 3.43 to 3.56 (m, 4H); 7.12 (s, 1H); 7.30 to 7.39 (m, 3H); from 7.55 to 7.63 (m, 2H); 7.95 (m, 2H); 8.07 (m, 3H); 8.75 (d, 1H). M + H = 386. |
| 17 | 207-209 | $^1$H NMR (DMSO) δ (ppm): 2.85 (d, 3H); 7.00 (s, 1H); from 7.25 to 7.35 (m, 2H); 7.41 (d, 1H); from 7.54 to 7.68 (m, 2H); 7.93 (d, 1H); 8.00 (d, 1H); 8.17 (s, 1H); 8.28 (s, 1H); 8.60 (m, 1H); 8.92 (d, 1H). M + H = 364. |
| 18 | 195-197 | $^1$H NMR (DMSO) δ (ppm): 2.85 (d, 3H); 7.10 (s, 1H); from 7.32 to 7.43 (m, 3H); 7.48 (m, 1H); 7.65 (t, 1H); 7.91 (d, 1H); 7.99 (d, 1H); 8.18 (m, 2H); 8.28 (s, 1H); 8.60 (m, 1H); 8.87 (d, 1H). M + H = 346. |
| 19 | 220-222 | $^1$H NMR (DMSO) δ (ppm): 2.82 (d, 3H); 7.30 (s, 1H); 7.39 (d, 1H); 7.64 (t, 1H); from 7.84 to 7.95 (m, 3H); 8.00 (d, 1H); 8.13 (s, 1H); 8.27 (m, 3H); 8.60 (m, 1H); 8.85 (d, 1H). M + H = 396. |
| 20 | 264-266 | $^1$H NMR (DMSO) δ (ppm): 2.65 (d, 3H); 6.86 (d, 1H); 7.14 (s, 1H); 7.34 (m, 2H); from 7.48 to 7.59 (m, 4H); 7.66 (s, 1H); 8.09 (m, 2H); 8.23 (d, 1H); 8.72 (d, 1H). M + H = 346. |
| 21 | 208-210 | $^1$H NMR (DMSO) δ (ppm): 2.84 (d, 3H); 7.14 (s, 1H); 7.34 (m, 3H); 7.95 (m, 4H); 8.09 (m, 3H); 8.55 (d, 1H); 8.80 (d, 1H). M + H = 346. |
| 22 | 173-175 | $^1$H NMR (DMSO) δ (ppm): from 1.65 to 2.05 (m, 2H); from 3.40 to 3.70 (m, 4H); 4.32 (d, 1h); 5.00 (d, 1H); 7.11 (s, 1H); 7.32 (m, 3H); 7.60 (m, 2H); 7.93 (d, 2H); 8.08 (m, 3H); 8.77 (d, 1H). M + H = 402. |
| 23 | 210-212 | $^1$H NMR (DMSO) δ (ppm): 2.87 (d, 3H); 7.07 (s, 1H); 7.25 (t, 1H); from 7.38 to 7.48 (m, 2H); 7.63 (t, 1H); 7.91 (d, 1H); 7.98 (d, 1H); 8.18 (m, 2H); 8.28 (s, 1H); 8.60 (m, 1H); 8.87 (d, 1H). M + H = 364. |
| 24 | 212-214 | $^1$H NMR (DMSO) δ (ppm): 2.85 (d, 3H); 7.21 (s, 1H); 7.36 (d, 1H); 7.50 (d, 2H); 7.62 (t, 1H); 7.90 (d, 1H); 8.00 (d, 1H); 8.12 (s, 1H); 8.18 (d, 2H); 8.27 (s, 1H); 8.60 (d, 1H); 8.83 (d, 1H). MP = 211° C. M + H = 412. |
| 25 | 209-211 | $^1$H NMR (DMSO) δ (ppm): 2.87 (d, 3H); 7.21 (s, 1H); 7.39 (d, 1H); from 7.54 to 7.68 (m, 2H); 7.90 (d, 2H); 8.00 (d, 1H); from 8.04 to 8.13 (m, 2H); 8.27 (s, 1H); 8.60 (d, 1H); 8.83 (d, 1H). M + H = 364. |
| 26 | 230-232 | $^1$H NMR (DMSO) δ (ppm): 2.85 (d, 3H); 7.30 (m, 2H); 7.39 (d, 1H); 7.63 (t, 1H); 7.78 (m, 2H); 7.92 (d, 1H); 8.01 (d, 1H); 8.13 (s, 1H); 8.27 (s, 1H); 8.61 (d, 1H); 8.84 (d, 1H). M + H = 364. |
| 27 | 204-206 | $^1$H NMR (DMSO) δ (ppm): 2.85 (d, 3H); 7.26 (m, 2H); 7.37 (d, 1H); from 7.53 to 7.64 (m, 2H); 7.82 (d, 1H); 7.90 (d, 2H); 8.00 (d, 1H); 8.11 (s, 1H); 8.27 (s, 1H); 8.61 (d, 1H); 8.85 (d, 1H). M + H = 346. |
| 28 | 204-206 | $^1$H NMR (DMSO) δ (ppm): 2.38 (s, 3H); 2.85 (d, 3H); 7.10 (s, 1H); 7.31 (m, 3H); 7.62 (t, 1H); 7.90 (m, 3H); 7.98 (d, 1H); 8.08 (s, 1H); 8.29 (s, 1H); 8.61 (d, 1H); 8.81 (d, 1H). M + H = 342. |

TABLE 2-continued

| No. | m.p. ° C. | NMR/[M + H] |
|---|---|---|
| 29 | 211-213 | $^1$H NMR (DMSO) δ (ppm): 2.85 (d, 3H); 3.82 (s, 3H); 7.06 (d, 3H); 7.31 (d, 1H); 7.64 (t, 1H); 7.90 (d, 1H); 7.98 (m, 3H); 8.07 (s, 1H); 8.27 (s, 1H); 8.61 (d, 1H); 8.80 (d, 1H). M + H = 358. |
| 30 | 187-189 | $^1$H NMR (DMSO) δ (ppm): 2.28 (s, 3H); 2.32 (s, 3H); 2.86 (d, 3H); 7.10 (s, 1H); 7.28 (d, 1H); 7.31 (d, 1H); 7.64 (t, 1H); 7.75 (d, 1H); 7.81 (s, 1H); 7.90 (d, 1H); 7.99 (d, 1H); 8.07 (s, 1H); 8.26 (s, 1H); 8.62 (d, 1H); 8.80 (d, 1H). M + H = 356. |
| 31 | 252-254 | $^1$H NMR (DMSO) δ (ppm): 2.87 (d, 3H); 7.32 (s, 1H); 7.43 (d, 1H); 7.63 (t, 1H); 7.92 (d, 1H); 8.00 (m, 3H); 8.15 (s, 1H); 8.27 (m, 3H); 8.62 (d, 1H); 8.87 (d, 1H). M + H = 353. |
| 32 | 214-216 | $^1$H NMR (DMSO) δ (ppm): 2.85 (d, 3H); 7.13 (s, 1H); from 7.32 to 7.43 (m, 2H); 7.50 (m, 1H); 7.63 (t, 1H); 7.90 (d, 1H); 7.97 (m, 2H); 8.17 (s, 1H); 8.27 (s, 1H); 8.60 (d, 1H); 8.88 (d, 1H). M + H = 364. |
| 33 | 129-131 | $^1$H NMR (DMSO) δ (ppm): 2.55 (s, 3H); 2.85 (d, 3H); 6.93 (s, 1H); 7.35 (m, 4H); 7.63 (t, 1H); 7.72 (m, 1H); 7.90 (d, 1H); 8.00 (d, 1H); 8.10 (s, 1H); 8.27 (s, 1H); 8.61 (d, 1H); 8.83 (d, 1H). M + H = 342. |
| 34 | 221-223 | $^1$H NMR (DMSO) δ (ppm): 2.88 (d, 3H); 7.42 (m, 2H); 7.47 (dd, 1H); 7.64 (t, 1H); 7.93 (m, 1H); 8.01 (m, 1H); 8.05 (m, 1H); 8.10 (m, 2H); 8.31 (m, 1H); 8.63 (m, 1H); 8.88 (d, 1H). M + H = 380 |

The compounds according to the invention underwent pharmacological tests for determining their modulatory effect on NOT.

Evaluation of the In Vitro Activity on N2A Cells

The activity of the compounds according to the invention was evaluated on a cell line (N2A) endogenously expressing the murine Nurr1 receptor and stably transfected with the NOT binding response element (NBRE) coupled to the luciferase reporter gene. The tests were performed according to the procedure described hereinbelow.

The cell line Neuro-2A is obtained from a standard commercial source (ATCC). The clone Neuro-2A was obtained from a spontaneous tumour originating from a strain of albino mice A by R. J Klebe et al. This line Neuro-2A is then stably transfected with 8NBRE-luciferase. The N2A-8NBRE cells are cultured to the point of confluence in 75 $cm^2$ culture flasks containing DMEM supplemented with 10% foetal calf serum, 4.5 g/L of glucose and 0.4 mg/ml of geneticin. After culturing for one week, the cells are recovered with 0.25% trypsin for 30 seconds and then resuspended in DMEM without phenol red, containing 4.5 g/L of glucose and 10% Hyclone defatted serum, and placed in white, transparent-base 96-well plates. The cells are deposited at a rate of 60 000 per well in 75 4, for 24 hours before adding the products. The products are applied in 25 4 and incubated for a further 24 hours. On the day of measurement, an equivalent volume (100 4) of Steadylite is added to each well, and the wells are then left for 30 minutes to obtain complete lysis of the cells and maximum production of the signal. The plates are then measured in a microplate luminescence counter, after having been sealed with an adhesive film. The products are prepared in the form of a $10^{-2}$ M stock solution, and then diluted in 100% of DMSO. Each concentration of product is prediluted in culture medium before incubation with the cells thus containing 0.625% final of DMSO.

The best compounds have an EC50 value of between 0.1 nM and 10 μM.

For example, compounds 2, 4, 10, 14, 16 and 26 have shown an EC50 value of 45; 2; 6.6; 125; 326 and 1.3 nM, respectively.

It is thus seen that the compounds according to the invention have a modulatory effect on NOT.

The compounds according to the invention may thus be used for the preparation of medicaments for their therapeutic application in the treatment or prevention of diseases involving the NOT receptors.

Thus, according to another of its aspects, a subject of the invention is medicaments that comprise a compound of formula (I) or an addition salt thereof with a pharmaceutically acceptable acid.

These medicaments find their therapeutic use especially in the treatment and prevention of neurodegenerative diseases, for instance Parkinson's disease, Alzheimer's disease, tauopathies (e.g. progressive supranuclear palsy, frontotemporal dementia, corticobasal degeneration, Pick's disease); cerebral trauma, for instance ischaemia and cranial trauma and epilepsy; psychiatric diseases, for instance schizophrenia, depression, substance dependency, and attention-deficit hyperactivity disorder; inflammatory diseases of the central nervous system, for instance multiple sclerosis, encephalitis, myelitis and encephalomyelitis and other inflammatory diseases, for instance vascular pathologies, atherosclerosis, joint inflammations, arthrosis, rheumatoid arthritis; osteoarthritis, Crohn's disease, ulcerative colitis; allergic inflammatory diseases such as asthma, autoimmune diseases, for instance type 1 diabetes, lupus, scleroderma, Guillain-Barré syndrome, Addison's disease and other immune-mediated diseases; osteoporosis; cancers.

These compounds may also be used as a treatment combined with grafts and/or transplantations of stem cells.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof, may be administered in unit administration form, as a mixture with standard pharmaceutical excipients, to man and animals for the prophylaxis or treatment of the above complaints or diseases.

The appropriate unit follus of administration include oral forms such as tablets, soft or hard gel capsules, powders, granules and oral solutions or suspensions, sublingual, buccal, intratracheal, intraocular, intranasal or inhalation administration forms, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Corn starch | 15.0 mg |

-continued

| | |
|---|---|
| Hydroxypropylmethylcellulose | 2.25 mg |
| Magnesium stearate | 3.0 mg |

There may be particular cases in which higher or lower dosages are appropriate; such dosages are not outside the context of the invention. According to the usual practice, the dosage that is appropriate for each patient is determined by the doctor according to the mode of administration and the weight and response of the said patient.

According to another of its aspects, the present invention also relates to a method for treating the pathologies indicated above, which comprises the administration, to a patient, of an effective dose of a compound according to the invention, or a pharmaceutically acceptable salt thereof.

The invention claimed is:

1. A compound of formula (I):

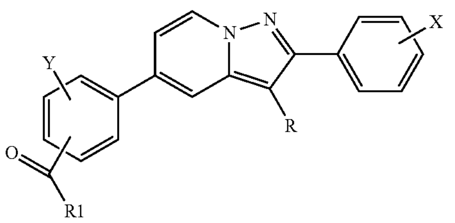

(I)

in which:

R represents a hydrogen or halogen atom or a group (C1-C6)alkyl;

X represents one or more substituents chosen from a hydrogen or halogen atom and a group (C1-C6)alkyl, halo(C1-C6)alkyl, (C1-C6)alkoxy, halo(C1-C6)alkoxy, cyano, hydroxyl or hydroxy(C1-C6)alkyl;

Y represents a hydrogen or halogen atom or a group (C1-C6)alkyl;

R1 represents a group NR2R3 or OR4;

R2 and R3 represent, independently of each other, a hydrogen atom or a group (C1-C6)alkyl, hydroxy(C1-C6) alkyl or oxo(C1-C6)alkyl, or alternatively R2 and R3 form, with the nitrogen atom that bears them, a heterocycle optionally substituted with a group (C1-C6)alkyl, hydroxyl or oxo, R4 represents a group (C1-C6)alkyl, hydroxy(C1-C6)alkyl or oxo(C1-C6)alkyl, in the form of base or of acid-addition salt.

2. The compound according to claim 1, wherein

R represents a hydrogen or chlorine atom,

X represents one or more substituents chosen from a halogen atom and a group (C1-C6)alkyl, halo(C1-C6)alkyl, (C1-C6)alkoxy, halo(C1-C6)alkoxy or cyano, Y represents a hydrogen atom, a halogen atom or a group (C1-C6)alkyl;

R1 represents a group OR4,

R4 represents a methyl group, in the form of base or of acid-addition salt.

3. The compound according to claim 1, wherein

R represents a hydrogen or chlorine atom,

X represents one or more substituents chosen from a chlorine or fluorine atom and a methyl, trifluoromethyl, methoxy, trifluoromethoxy or cyano group, Y represents a hydrogen, chlorine or fluorine atom or a methyl group, R1 represents a group OR4, R4 represents a methyl group, in the form of base or of acid-addition salt.

4. The compound according to claim 1, wherein

R represents a hydrogen or chlorine atom,

X represents one or more substituents chosen from a halogen atom and a group (C1-C6)alkyl, halo(C1-C6)alkyl, (C1-C6)alkoxy, halo(C1-C6)alkoxy or cyano, Y represents a hydrogen atom, a halogen atom or a group (C1-C6)alkyl;

R1 represents a group NR2R3,

R2 and R3 represent, independently of each other, a hydrogen atom or a methyl, ethyl, isopropyl or cyclopropyl group, or alternatively R2 and R3 form, with the nitrogen atom that bears them, a morpholinyl or pyrrolidinyl group optionally substituted with a hydroxyl group, in the form of base or of acid-addition salt.

5. The compound according to claim 1, wherein

R represents a hydrogen or chlorine atom,

X represents one or more substituents chosen from a chlorine or fluorine atom and a methyl, trifluoromethyl, methoxy, trifluoromethoxy or cyano group, Y represents a hydrogen or chlorine atom or a methyl group, R1 represents a group NR2R3, R2 and R3 represent, independently of each other, a hydrogen atom or a methyl, ethyl, isopropyl or cyclopropyl group, or alternatively R2 and R3 form, with the nitrogen atom that bears them, a morpholinyl or pyrrolidinyl group optionally substituted with a hydroxyl group, in the form of base or of acid-addition salt.

6. The compound according to claim 1 corresponding to the following formulae:

Methyl 3-[2-(4-chlorophenyl)pyrazolo[1,5-α]pyridin-5-yl]benzoate

3-[2-(4-Chlorophenyl)pyrazolo[1,5-α]pyridin-5-yl]benzamide

3-[2-(4-Chlorophenyl)pyrazolo[1,5-α]pyridin-5-yl]-N,N-dimethylbenzamide

3-[2-(4-Chlorophenyl)pyrazolo[1,5-α]pyridin-5-yl]-N-methylbenzamide

Methyl 3-[2-(4-fluorophenyl)pyrazolo[1,5-α]pyridin-5-yl]benzoate

3-[2-(4-Fluorophenyl)pyrazolo[1,5-α]pyridin-5-yl]-N-methylbenzamide

3-[2-(4-Fluorophenyl)pyrazolo[1,5-α]pyridin-5-yl]-N-isopropylbenzamide

3-[2-(4-Fluorophenyl)pyrazolo[1,5-α]pyridin-5-yl]-N,N-dimethylbenzamide

{3-[2-(4-Fluorophenyl)pyrazolo[1,5-α]pyridin-5-yl]phenyl}morpholin-4-yl-methanone 3-[2-(4-Fluorophenyl)pyrazolo[1,5-α]pyridin-5-yl]-2,N-dimethylbenzamide 2-Chloro-5-[2-(4-fluorophenyl)pyrazolo[1,5-α]pyridin-5-yl]-N-methylbenzamide 4-Chloro-3-[2-(4-fluorophenyl)pyrazolo[1,5-α]pyridin-5-yl]-N-methylbenzamide 3-[2-(4-Fluorophenyl)pyrazolo[1,5-α]pyridin-5-yl]-4,N-dimethylbenzamide 2-Fluoro-4-[2-(4-fluorophenyl)pyrazolo[1,5-α]pyridin-5-yl]-N-methylbenzamide N-Cyclopropyl-3-[2-(4-fluorophenyl)pyrazolo[1,5-α]pyridin-5-yl]benzamide {3-[2-(4-Fluorophenyl)pyrazolo[1,5-α]pyridin-5-yl]phenyl}pyrrolidin-1-ylmethanone 3-[2-(2,6-Difluorophenyl)pyrazolo[1,5-α]pyridin-5-yl-methylbenzamide 3-[2-(2-Fluorophenyl)pyrazolo[1,5-α]pyridin-5-yl]-N-methylbenzamide N-Methyl-3-[2-(4-trifluoromethylphenyl)pyrazolo[1,5-α]pyridin-5-yl]benzamide 4-[2-(4-Fluorophenyl)pyrazolo[1,5-α]pyridin-5-yl]-N-methylbenzamide 2-[2-(4-Fluorophenyl)pyrazolo[1,5-α]pyridin-5-yl]-N-methylbenzamide {3-[2-(4-Fluorophenyl)pyrazolo[1,5-α]pyridin-5-yl]phenyl}-(3-hydroxypyrrolidin-1-yl)methanone 3-[2-(2,4-Difluorophenyl)pyrazolo[1,5-α]pyridin-5-yl]-N-methylbenzamide N-Methyl-3-[2-(4-trifluoromethoxyphenyl)pyrazolo[1,5-α]pyridin-5-yl]benzamide 3-[2-(3,4-Difluorophenyl)pyrazolo[1,5-α]pyridin-5-yl]-N-methylbenzamide 3-[2-(3,5-Difluorophenyl)pyrazolo[1,5-α]pyridin-5-yl]-N-methylbenzamide 3-[2-(3-Fluorophenyl)pyrazolo[1,5-α]pyridin-5-yl]-N-methylbenzamide N-Methyl-3-(2-p-tolylpyrazolo[1,5-α]pyridin-5-yl)benzamide 3-[2-(4-Methoxyphenyl)pyrazolo[1,5-α]pyridin-5-yl]-N-methylbenzamide 3-[2-(3,4-Dimethylphenyl)pyrazolo[1,5-α]pyridin-5-yl]-N-methylbenzamide 3-[2-(4-Cyanophenyl)pyrazolo[1,5-α]pyridin-5-yl]-N-methylbenzamide 3-[2-(2,3-Difluorophenyl)pyrazolo[1,5-α]pyridin-5-yl]-N-methylbenzamide N-Methyl-3-(2-o-tolylpyrazolo[1,5-α]pyridin-5-yl)benzamide 3-[3-Chloro-2-(4-fluorophenyl)pyrazolo[1,5-α]pyridin-5-yl]-N-methylbenzamide.

7. A pharmaceutical composition comprising the compound of claim 1, or an addition salt of said compound with a pharmaceutically acceptable acid.

8. The pharmaceutical composition of claim 7 further comprising at least one pharmaceutically acceptable excipient.

* * * * *